United States Patent
Likuski et al.

(10) Patent No.: US 8,733,152 B2
(45) Date of Patent: May 27, 2014

(54) AUTOMATED ANALYZER WITH LOW-PRESSURE IN-LINE FILTRATION

(75) Inventors: Robert Likuski, Walnut Creek, CA (US); Donald Bartling, Novato, CA (US); Yao Kunquan, San Francisco, CA (US); Tong Le, Pinole, CA (US); Kent Matsumoto, Kensington, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 148 days.

(21) Appl. No.: 13/007,284

(22) Filed: Jan. 14, 2011

(65) Prior Publication Data

US 2012/0103074 A1 May 3, 2012

Related U.S. Application Data

(60) Provisional application No. 61/296,177, filed on Jan. 19, 2010.

(51) Int. Cl.
*G01N 1/00* (2006.01)
*G01N 13/00* (2006.01)
*G01N 30/02* (2006.01)

(52) U.S. Cl.
USPC .................. 73/61.56; 73/61.55; 436/161

(58) Field of Classification Search
CPC ....... G01N 30/06; G01N 30/16; G01N 30/34; G01N 30/40
USPC .................. 73/61.55, 61.56, 64.56; 436/161
See application file for complete search history.

(56) References Cited

U.S. PATENT DOCUMENTS

| | | | |
|---|---|---|---|
| 5,468,643 A | 11/1995 | Su et al. | |
| 5,624,537 A | 4/1997 | Turner et al. | |
| 5,888,401 A | 3/1999 | Nguyen | |
| 5,919,988 A * | 7/1999 | Pazos et al. | 568/679 |
| 5,933,357 A | 8/1999 | Tipler | |
| 6,265,226 B1 * | 7/2001 | Petro et al. | 506/12 |
| 6,923,865 B2 | 8/2005 | Serafin et al. | |
| 2002/0020670 A1* | 2/2002 | Petro | 210/656 |
| 2004/0235187 A1* | 11/2004 | LaCourse et al. | 436/177 |

(Continued)

FOREIGN PATENT DOCUMENTS

| | | |
|---|---|---|
| EP | 0 259 259 A2 | 3/1988 |
| EP | 0 341 824 A2 | 11/1989 |

(Continued)

OTHER PUBLICATIONS

Kuffner, Hu. Jun 1999. "Fully Automatic Measurement of Active Substance Release from Pharmaceuticals," *GIT Labor-Fachz.*, pp. 606-609.

(Continued)

*Primary Examiner* — Hezron E Williams
*Assistant Examiner* — Nathaniel Kolb
(74) *Attorney, Agent, or Firm* — Kilpatrick Townsend & Stockton LLP

(57) ABSTRACT

An automated analyzer for biological samples that contain particulate matter is adapted to be able to process a large number of samples without changing the analytical cartridge, and in many cases without changing the internal switching valves, by including a filter in the low-pressure section of the analyzer, and preferably configuring the analyzer to be able to perform backflushing on the filter between sample injections.

26 Claims, 12 Drawing Sheets

(56) References Cited

U.S. PATENT DOCUMENTS

| | | | |
|---|---|---|---|
| 2005/0092685 A1* | 5/2005 | Hilhorst et al. | 210/656 |
| 2006/0037911 A1* | 2/2006 | Dasgupta et al. | 210/656 |
| 2006/0213823 A1* | 9/2006 | Rigoli | 210/198.2 |
| 2007/0240497 A1* | 10/2007 | Robinson et al. | 73/61.41 |
| 2007/0281361 A1* | 12/2007 | Hariharan | 436/89 |

FOREIGN PATENT DOCUMENTS

| | | | | |
|---|---|---|---|---|
| JP | 62-108155 A | 5/1987 | | |
| JP | H01-262911 A | 10/1989 | | |
| JP | H02-164423 A | 6/1990 | | |
| JP | 10031010 A | * | 2/1998 | G01N 30/26 |
| JP | 2009-136170 A | 6/2009 | | |
| WO | 2006/080761 A1 | 8/2006 | | |

OTHER PUBLICATIONS

Office Action from JP Appl. No. 2012-549158, dated Nov. 5, 2013.

* cited by examiner

AUTOMATED ANALYZER WITH LOW-PRESSURE IN-LINE FILTRATION

CROSS-REFERENCE TO RELATED APPLICATION

This application claims the benefit of U.S. Provisional Patent Application No. 61/296,177, filed Jan. 19, 2010, the contents of which are incorporated herein by reference.

BACKGROUND OF THE INVENTION

1. Field of the Invention

This invention resides in the field of automated analyzers for biological samples.

2. Description of the Prior Art

The analysis of biological fluids such as blood, urine, tissue extracts, and the like is often done on a large number of samples and by methods that involve comparisons among samples and against standards. A high degree of precision is needed, particularly when the sample contains a variety of competing species that can interfere with obtaining proper analytical results. Automated analyzers are well adapted to use on large numbers of samples and to the performance of analyses in a repetitive and uniform manner. In addition to providing convenience and economy, automated analyzers eliminate the variations that frequently occur when analyses are performed manually, and particularly by different individuals.

One of the difficulties with automated systems is the need to remove debris from the samples before the samples enter the critical analytical components such as chromatographic columns and detectors. This is particularly true for blood samples, which are first treated by hemolysis to liberate the species of interest and the proteins in general before entering the analytical system. The types of sample debris that are present in the hemolysate include cell wall fragments and other particulates as well as lipids. All such debris enters the system during the sample preparation and handling.

The removal of sample debris is particularly important in automated systems that utilize high-pressure units such as high-performance liquid chromatography (HPLC) to separate the sample components for purposes of identification and quantification and those that contain switching valves that are used in the automated sequences of sample handling. Once the contamination in these components reaches a degree where the analysis is impaired, the analyzer must be shut down and opened so that the contaminated part, whether it be an analytical column or an internal valve, can be removed and either cleaned or replaced. The time consumed in performing these tasks and the lost usage time of the instrument can be costly. Also, the possibility of errors occurring before the shutdown casts uncertainty on the reliability of the instrument and on the accuracy of the analyses already performed.

SUMMARY OF THE INVENTION

The present invention addresses the problems enumerated above by incorporating a sample filter in a low-pressure section of the analyzer, rather than in a section that operates under the high pressure used in the analytical column. An analyzer of this invention thus includes a low-pressure section by which the sample is introduced into the analyzer and in many cases prepared for analysis, a high-pressure section designed to provide high-pressure pumping of sample through the analytical cartridge, an analytical section that includes the analytical cartridge and a sample loop, and a switching valve that connects the analytical section to either the low-pressure section or the high-pressure section. A sample of biological fluid is thus analyzed, in accordance with this invention, by introducing the sample into the low-pressure section, pumping the sample from the low-pressure section through the sample filter to fill the sample loop by way of the low-pressure pump, pumping the sample from the sample loop to the analytical cartridge and through the cartridge by way of the high-pressure pump, and detecting the components of the sample that were separated in the cartridge. In certain embodiments of this invention, the analyzer includes a sample dilution well, a sample transfer subsystem to add sample to the sample dilution well and to add diluent to the well to dilute the sample, an analytical cartridge subsystem including a sample loop and an analytical cartridge, a low-pressure pump system to pump sample from the sample dilution well into the sample loop at low pressure, a high-pressure pump system to pump buffer liquid through the sample loop and the analytical cartridge at high pressure to achieve the separation in the cartridge, and a multi-position switching valve that switches between various positions including a position for the low-pressure priming of the sample loop and a position for the high-pressure purging of the sample loop with buffer liquid to transfer sample from the sample loop to the analytical cartridge where separation of the sample components occurs. The sample filter is positioned between the sample dilution well and the sample loop at a site that is maintained at the low pressure of the low-pressure pump subsystem regardless of the position of the multi-position switching valve, i.e., during both priming of the sample loop and passage of the sample through the analytical cartridge. With a sample filter in this low-pressure section, the analyzer can be used on many more samples without the need for removing and replacing the analytical cartridge. In certain embodiments of the invention, the multi-position switching valve has a backflushing position in addition to the two positions described above, to permit automated backflushing. In certain embodiments as well, the sample filter is positioned between the sample dilution well and all valves that are downstream of the well, i.e., in the direction leading to the analytical cartridge. These features provide even further increases in the number of samples that can be run through the instrument without compromising the reliability and accuracy of the results. These and other objects, features, and advantages of the invention are explained in detail below.

DESCRIPTION OF ILLUSTRATIVE EMBODIMENTS

Figure 1:
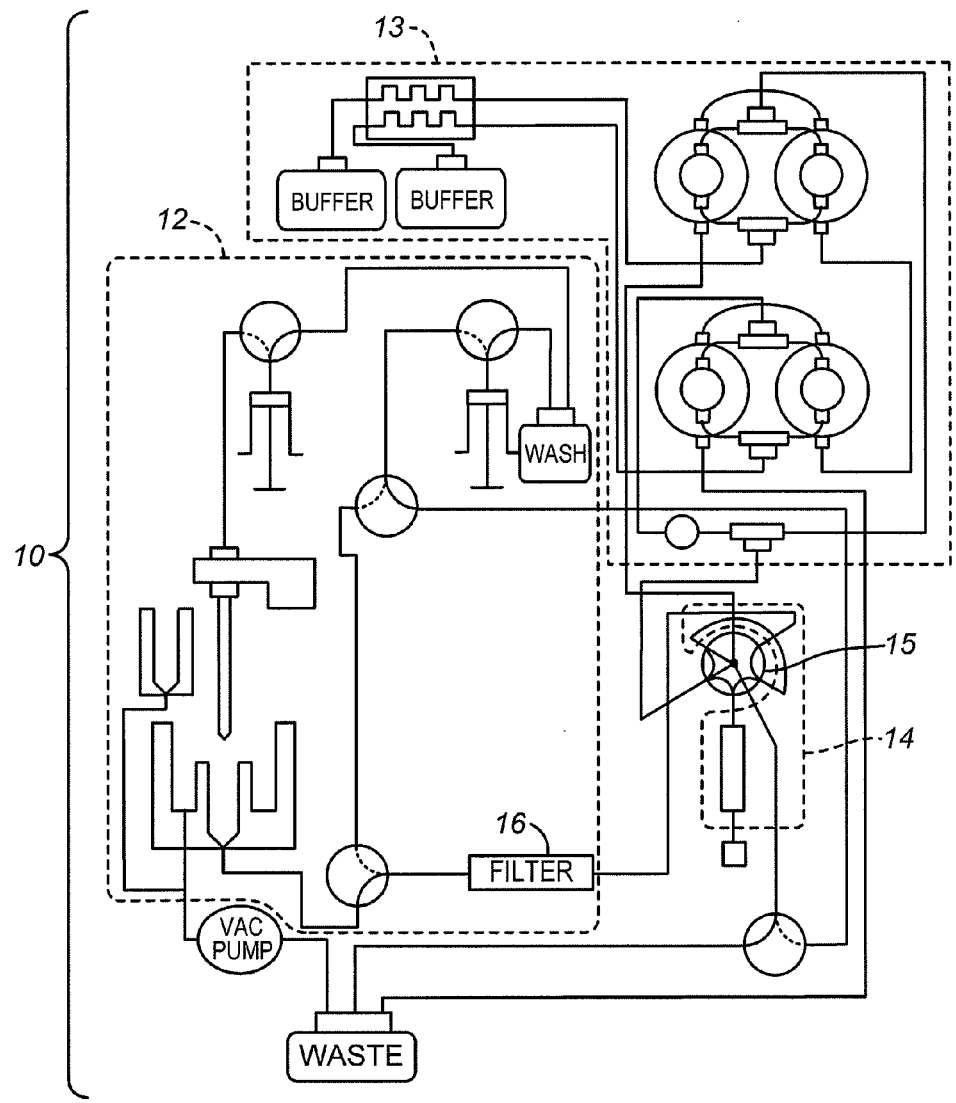
FIG. 1 is a diagram of the flow system architecture of an analyzer in accordance with the present invention.

FIG. 1 is a diagram of the flow system architecture for one example of an automated blood sample analyzer 10 in accordance with the present invention. Three sections are outlined in dashed lines: a low-pressure section 12, a high-pressure section 13, and an analytical section 14. A switching valve 15 is also shown, and a sample filter 16 is shown in the low-pressure section 12.

Figure 2:
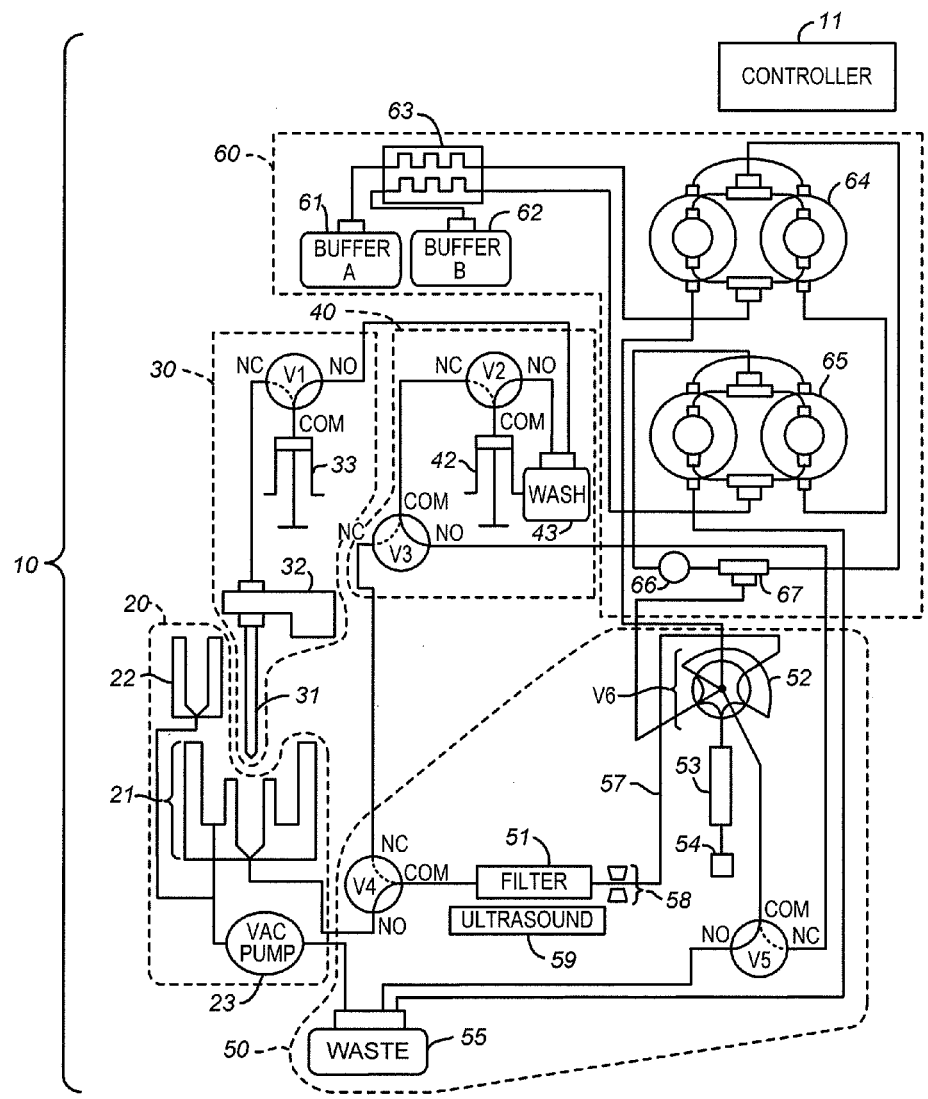
FIG. 2 is another diagram of the analyzer of FIG. 1, with the components shown in alternate groupings for purposes of further illustration.

The flow system is shown in greater detail in FIG. 2 where the analyzer components are grouped into subsystems and a controller 11 which controls all valves, sensors, pumps, and detectors of the analyzer is included. The subsystems include a sample dilution subsystem 20, a sample transfer, or needle, subsystem 30, a low-pressure pump subsystem 40, an analytical cartridge subsystem 50, and a high-pressure pump subsystem 60. The controller 11 can be a general purpose computer, a purpose-built computer, or a remote server. The controller 11 in this example includes both hardware and software, and can be part of the analyzer 10 itself or a separate system. The analyzer 10 contains several subsystems, including those listed in the "SUMMARY OF THE INVENTION" section above and others. The subsystems are outlined in dashed lines in the Figure and described below.

In the dilution subsystem 20, the sample is diluted with a diluent prior to entry of the sample into the analytical column. The dilution subsystem includes a dilution well 21, a needle wash well 22, and a vacuum pump 23 to transfer waste fluids from the dilution well 21 or the needle wash well 22 to a waste container 55.

The sample transfer, or needle, subsystem 30 draws a sample from a sample receptacle (not shown) and transfers the sample to the dilution well 21. The needle subsystem includes a needle 31 and a mobile needle arm 32 that moves the needle between the sample receptacle and the dilution well 21. The needle arm 32 is either manually manipulated by the user or robotically manipulated through the controller 11. The needle subsystem also includes a three-way transition valve V1 and a low-pressure pump 33. An example of a low-pressure pump useful for this purpose is a syringe pump that can both draw liquid in one direction toward the pump, for example from the sample reservoir, and push liquid in the reverse direction away from the pump, for example into the dilution well 21. An example of a transition valve is a solenoid-operated three-way valve. This valve V1 and all other three-way valves in the system shown, including all of its subsystems, each contain three connections, i.e., the common connection (labeled "COM") which is always open, the normally open connection (labeled "NO") which is open when the solenoid is not energized, and the normally closed connection (labeled "NC") which is closed when the solenoid is not energized. In the non-operational mode shown in FIG. 1 and in each of the stages shown in the succeeding figures, the lines of flow through the valves that are open are represented by solid lines, and the lines that are closed are represented by dashed lines. The low-pressure pump 33 is connected to the common connection COM of the transition valve V1.

The low-pressure pump subsystem 40 includes a low-pressure pump 42, a reservoir for wash fluid 43, which also serves as the diluent used in the dilution subsystem 20, and two three-way valves V2, V3. The low-pressure pump 42 is connected to the common connection COM of one three-way valve V2, and one of the other mobile connections of the same valve V2 is connected to the common connection COM of the other three-way valve V3. Here again, the low-pressure pump 42 is illustrated by a syringe pump that can both draw wash fluid into the pump from the wash fluid reservoir 43 and expel wash fluid from the pump into the transfer lines in the other subsystems, including backflushing the low-pressure filter (as described below). Separate lines from the wash fluid reservoir 43 lead to the low pressure pump 42 of the pump subsystem through the three-way valve V2 and to the low-pressure pump 33 of the needle subsystem through the three-way valve V1.

The analytical cartridge subsystem 50 includes the low-pressure sample filter 51 (this filter serves as a prefilter and is the same as the sample filter 16 of FIG. 1), two three-way valves V4, V5, an injection valve V6, a sample loop 52, the analytical cartridge 53, a detector 54, and a waste receptacle 55. The sample filter 51 is directly downstream of both the dilution subsystem 20 and the low-pressure pump subsystem 40, and is connected to the common connection COM of the first three-way valve V4. The filter output line 57 leads directly to the injection valve V6. Two accessory components to enhance backflushing are also shown—a pinch valve 58 and an ultrasonic transducer 59. The pinch valve 58 is attached to the line 57 which is made of pliable material, and by periodically opening and closing over the pliable tubing, the valve produces pressure pulses in the backflushing fluid. The ultrasonic transducer 59 is, for example, a piezoelectric crystal stack ultrasonically coupled to the sample filter 51 through fluid surrounding the filter to transmit ultrasonic pressure waves to the filter.

Figure 3:
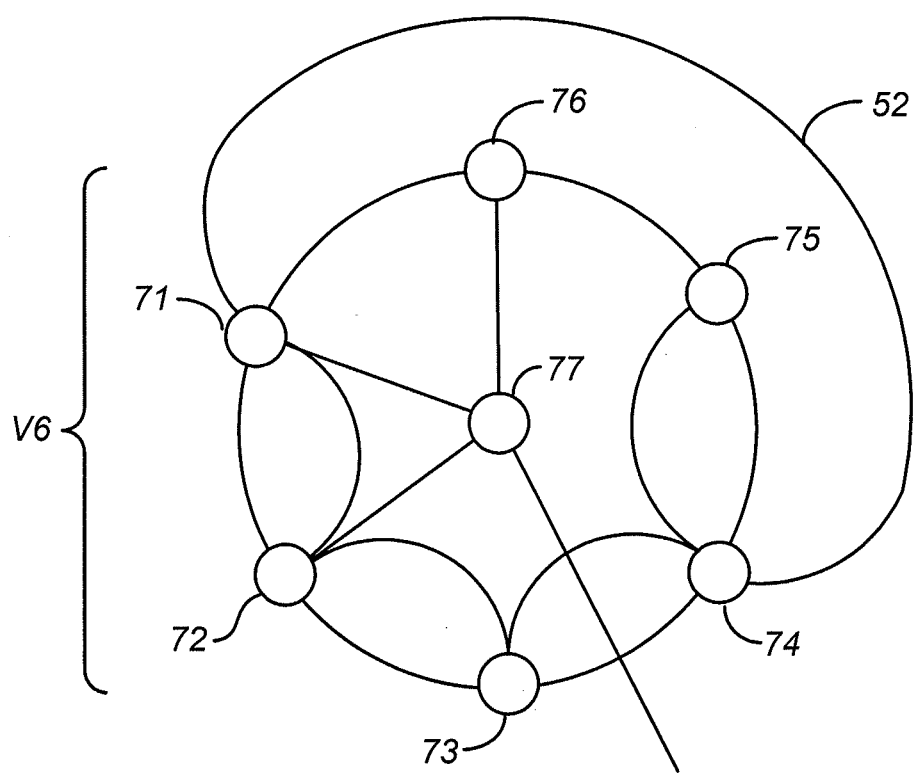
FIG. 3 is a diagram of a rotary valve for use as the multi-position switching valve in the analyzer of FIG. 2.

The injection valve V6 serves as the valve referred to in the "SUMMARY OF THE INVENTION" above as the "multi-position switching valve." One example of a valve that can be used for this purpose is a seven-port rotary valve shown in an enlarged representation in FIG. 3. The seven ports include six ports 71, 72, 73, 74, 75, 76 arranged in a circle and evenly spaced around the circle, and the seventh port 77 at the center of the circle. The various positions of the injection valve provide flow connections between eight pairs of the ports in various combinations, and the sample loop 52 is a length of tubing of predetermined volume (i.e., length and diameter) joining two of the seven ports. Another port is fluidly connected to the analytical cartridge 53.

Figure 4A:
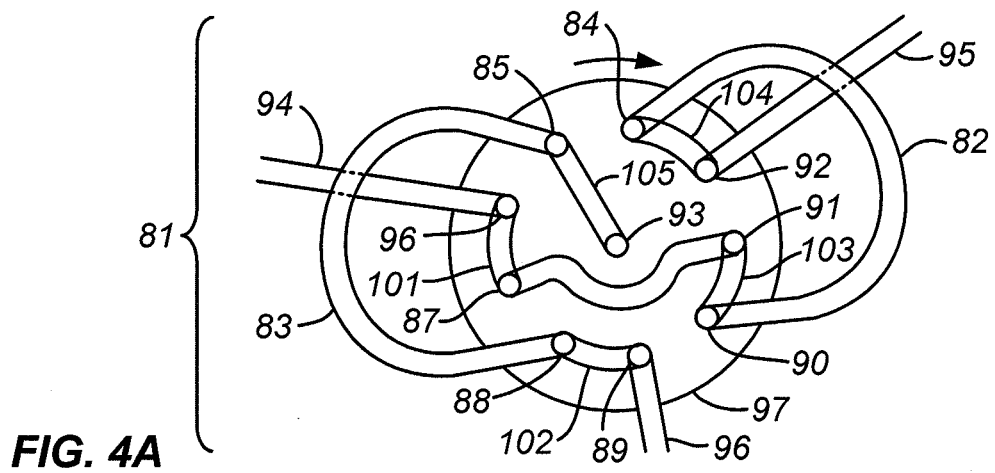
FIG. 4A is a diagram of a second rotary valve for use as an alternative to that of FIG. 2.
Figure 4B:
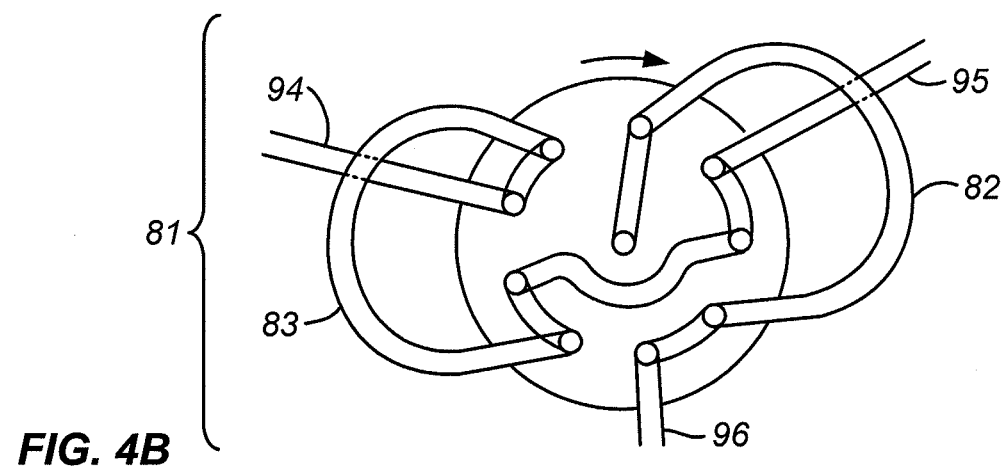
FIG. 4B is a diagram of the rotary valve of FIG. 3A upon rotation into a second position.
Figure 4C:
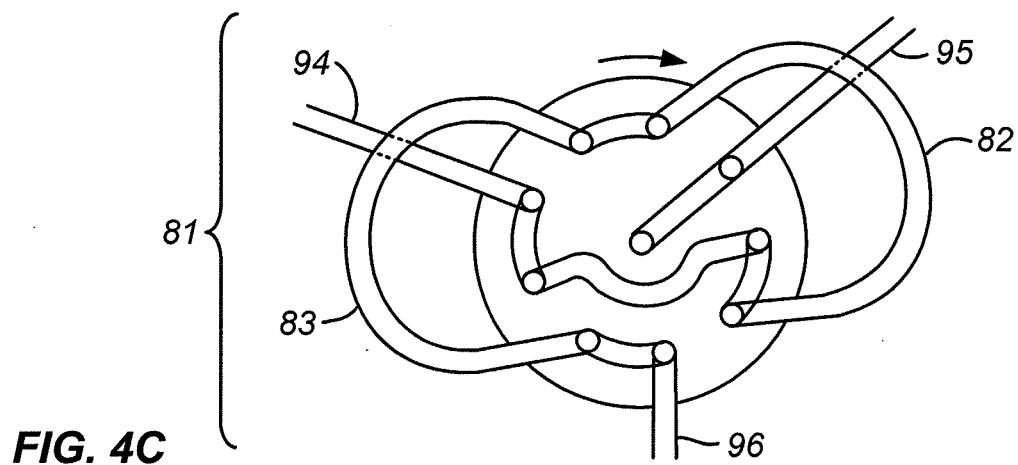
FIG. 4C is a diagram of the rotary valve of FIG. 3A upon rotation into a third position.

Another example of a "multi-position switching valve" that can be used as the injection valve V6 is the valve shown in FIGS. 4A, 4B, and 4C. The valve 81 in these figures is a ten-port rotary valve with two sample loops 82, 83. Nine of the ports 84, 85, 86, 87, 88, 89, 90, 91, 92 are arranged in a circle and are evenly spaced around the circle, and the tenth port 93 is at the center of the circle. Conduits leading to the various ports include a sample inlet line 94 fed by the high-pressure pump system, a sample outlet line 95 leading to the analytical cartridge, and a line 96 leading to waste. The central port 93 is connected to the wash fluid source. All ten ports and both sample loops are on the stationary portion of the valve. The rotary portion 97 of the valve contains five connecting passages. Four of the connecting passages 101, 102, 103, 104 are positioned to align with adjacent pairs of ports 84 through 92 in the circle, moving through the pairs as the valve rotates. The fifth connecting passage 105 is positioned to align with the center port 93 and each one of the ports 84 through 92 in the circle in succession as the valve rotates. In the position shown in FIG. 4A, the high-pressure pump system is connected to the first sample loop 82, causing the contents of the first sample loop 82 to be pumped through the outlet line 95 to the analytical cartridge. In the position shown in FIG. 4B, the high-pressure pump subsystem is connected to the second sample loop 83, causing the contents of the second sample loop 83 to be pumped through the outlet line 95 to the analytical cartridge, while wash fluid entering through the central port 93 flows through the first sample loop 82 and out the waste line 96. In the position shown in FIG. 4C, both sample loops 82, 83 are connected in series to the high-pressure pump subsystem so that when wash fluid is pumped by the high-pressure pump subsystem and enters the inlet line 94, the wash fluid passes through both sample loops and out the waste line 96.

Returning to FIG. 2, the high-pressure pump subsystem 60 includes two buffer receptacles 61, 62 for the separation buffer and the elution buffer, respectively, a degasser or debubbler 63 to remove dissolved gas, bubbles, or both from the buffer solutions, two high-pressure pumps 64, 65, a pressure sensor 66, and a T-junction 67 joining the outputs from the two high-pressure pumps. Fluid transfer lines variously join the buffer receptacles to the inlets to the high-pressure pumps through the degasser/debubbler 63, from the outputs from the high-pressure pumps 64, 65 to the T-junction 67, from the T-junction 67 to the injection valve V6 in the analytical cartridge subsystem 50. The pressure sensor 66 is located upstream of the T-junction 67 to minimize the fluid volume between the T-junction 67 and the injection valve V6.

FIGS. 5A through 5F are representations of the successive stages of a typical sequence followed in an analytical procedure using the analyzer of FIGS. 1 and 2, including the seven-port rotary injection valve of FIG. 3. It will be readily apparent to one skilled in the art as to how to adapt the stages to the use of the ten-port rotary invention valve of FIGS. 4A, 4B, and 4C.

Each of FIGS. 5A through 5F shows only the parts of the flow system architecture that are in use in the stage shown, together with the positions of the three-way and injection valves and the resulting fluid path. The sequence begins with FIG. 5A after a sample has been dispensed into the dilution well 21 by the needle subsystem and wash buffer has been added as a diluent. In this stage, a flow path is created by energizing transition valves V2 and V5 and by placing the injection valve V6 in a position that will connect port 75 to port 74 and port 71 to port 77. The three-way valves V3 and V4 are left unenergized, i.e., the fluid path passes through their normally open (NO) ports. With the various valves in these positions, a flow path is created between the dilution well 21 and the low-pressure pump 42 in the pump subsystem 40. The low-pressure pump 42 is activated in the direction shown by the downward arrow to draw the diluted sample from the dilution well 21 and into the analytical cartridge subsystem 50. The low-pressure filter 51 is the limit of the travel of the sample at this stage, due to the limited travel and limited suction capability of the low-pressure pump 42.

Figure 5A:
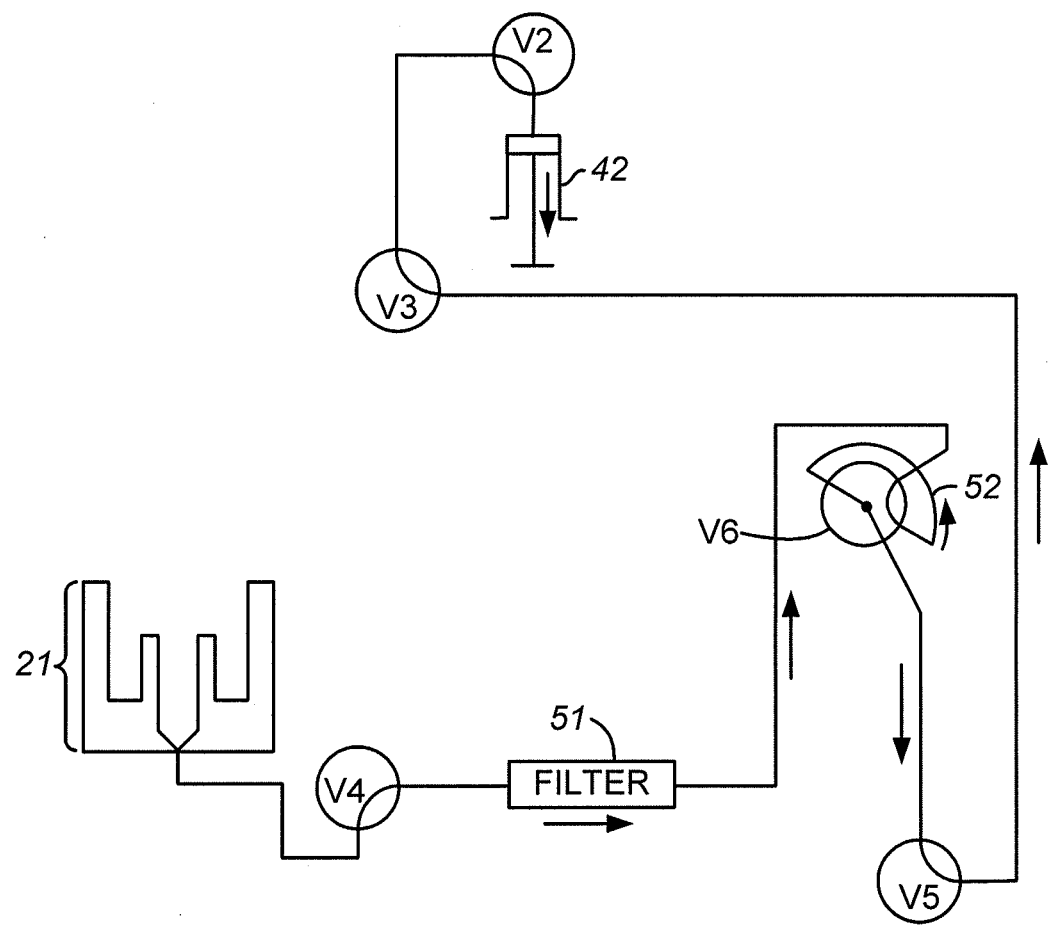
FIG. 5A is a diagram of the analyzer of FIG. 1 in a first stage of operation.
Figure 5B:
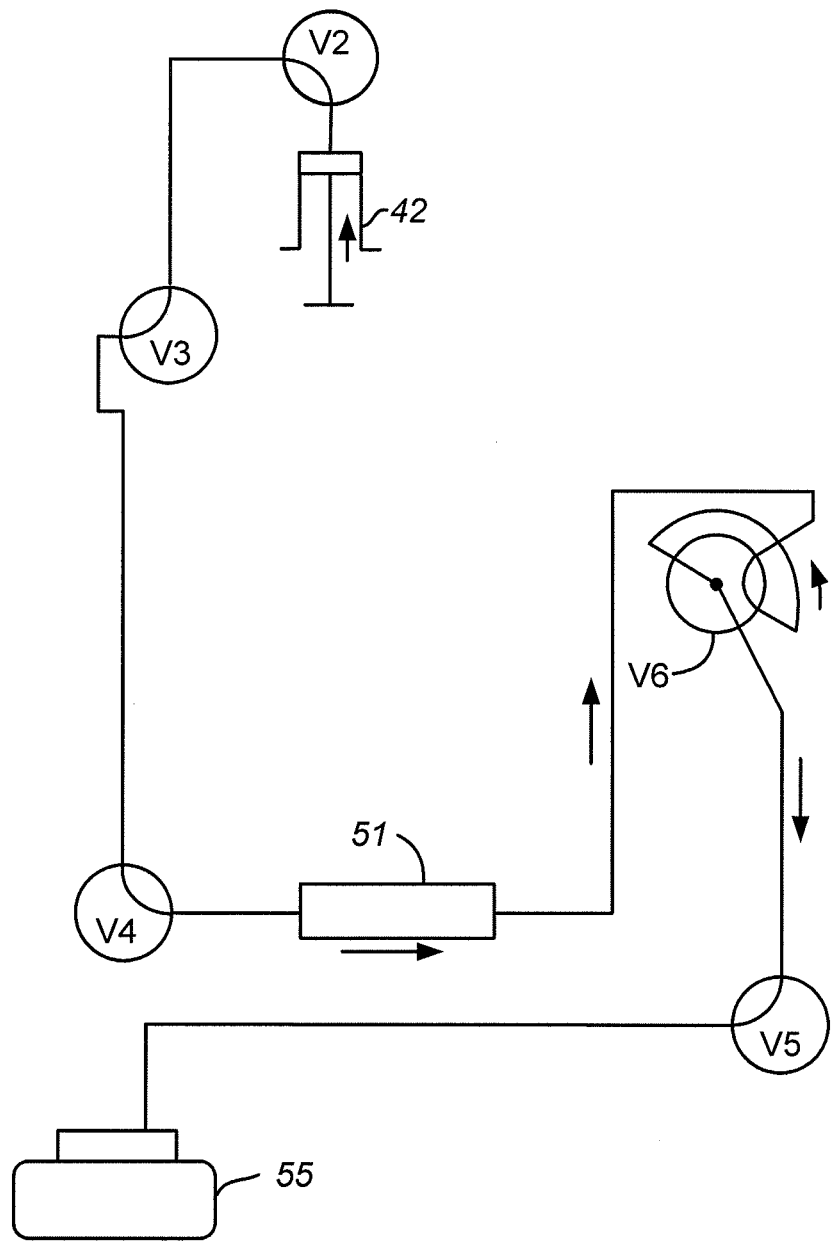
FIG. 5B is a diagram of the analyzer of FIG. 1 in a second stage of operation.

To advance the sample through the low-pressure filter 51 and into the sample loop 52, the system is placed in the configuration shown in FIG. 5B. In this flow configuration, the three-way valves V3 and V4 are energized and V5 is de-energized, and the injection valve V6 is rotated to a position that will connect only port 75 with port 74 and port 71 with port 77. The low-pressure pump 42 is then activated in the forward direction, as indicated by the upward arrow in the pump barrel, and the sample is pushed from upstream of the low-pressure filter 51 through the filter and into the sample loop 52.

Figure 5C:
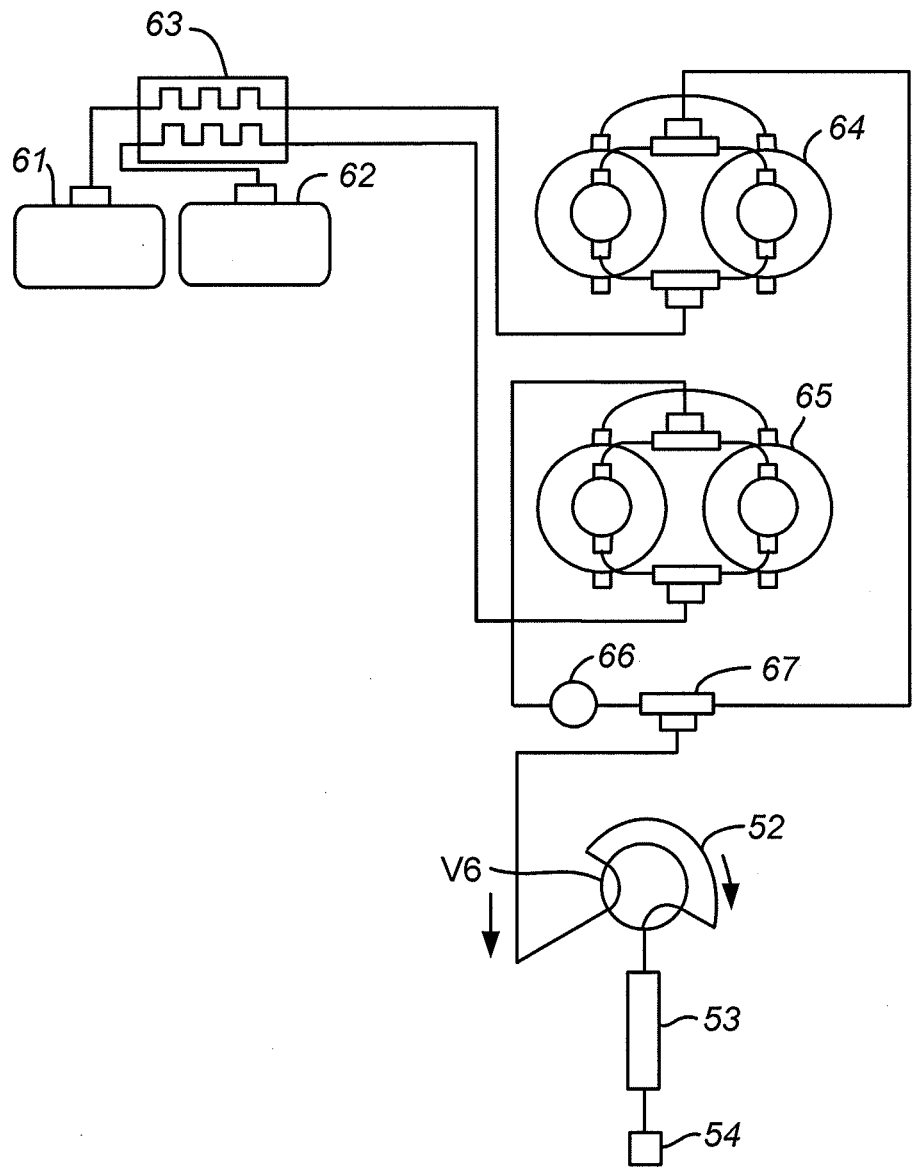
FIG. 5C is a diagram of the analyzer of FIG. 1 in a third stage of operation.

To perform an analysis on the sample, the valves are switched to positions that produce the flow path shown in FIG. 5C. In this flow path, the sample is pushed by the high-pressure pump subsystem 60 from the sample loop 52 through the analytical cartridge 53 and the detector 54. To form these flow paths, the injection valve V6 is rotated to the position in which the only ports connected are port 71 with port 72 and port 74 with port 73. Movement of the sample is achieved by a time-varying mixture of the buffers from reservoirs 61 and 62. The buffer in reservoir 61 is drawn by the first high-pressure pump 64 through the degasser/debubbler 63 and then forced into one connection of the mixing T-junction 67. Similarly, the buffer in reservoir 62 is drawn by the second high-pressure pump 65 and then forced into the other connection of the mixing T-junction 67. The mixture of the two buffers leaves the T-junction 67 by the remaining connection of the T-junction and then passes through the sample loop 52 and the analytical cartridge 53, and the separated components emerging from the cartridge pass through the detector 54. With an appropriately programmed variation of the proportions of the two buffers, as will be readily apparent to those skilled in chromatographic separations of the biological samples, the components of the sample that previously occupied the sample loop 52 are separated and individually detected, quantified, or both.

Figure 5D:
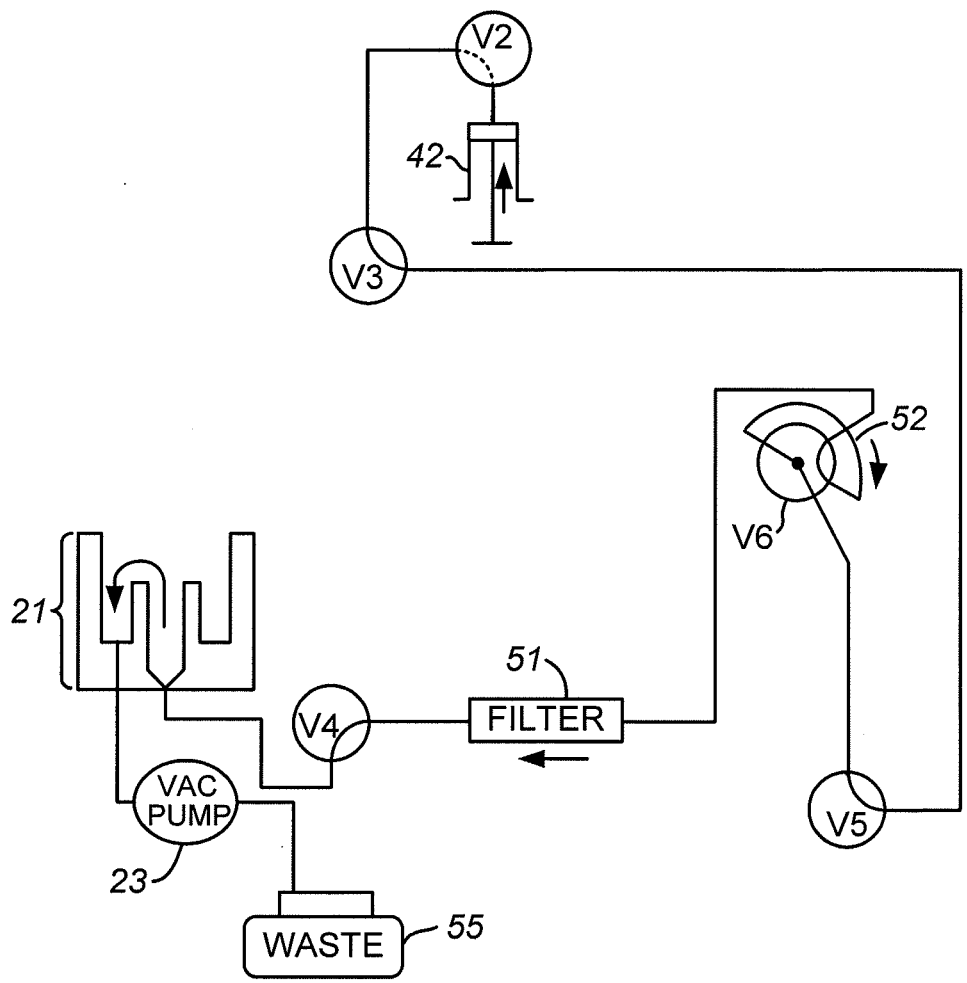
FIG. 5D is a diagram of the analyzer of FIG. 1 in a fourth stage of operation.

To backflush the various flow channels after a sample has been analyzed, the valves are switched to the configuration shown in FIG. 5D. The achieve this configuration, three-way valves V3 and V5 are energized, transition valve V4 is de-energized, and injection valve V6 is rotated to a position in which port 75 is connected to port 74 and port 71 is connected to port 77. Wash fluid has been drawn into the low-pressure pump 42, which is then activated in the forward direction, as indicated by the arrow shown in the valve interior. In this direction, the pump drives the wash fluid through the sample loop 52 and the prefilter 51, both in the reverse direction.

Figure 5E:
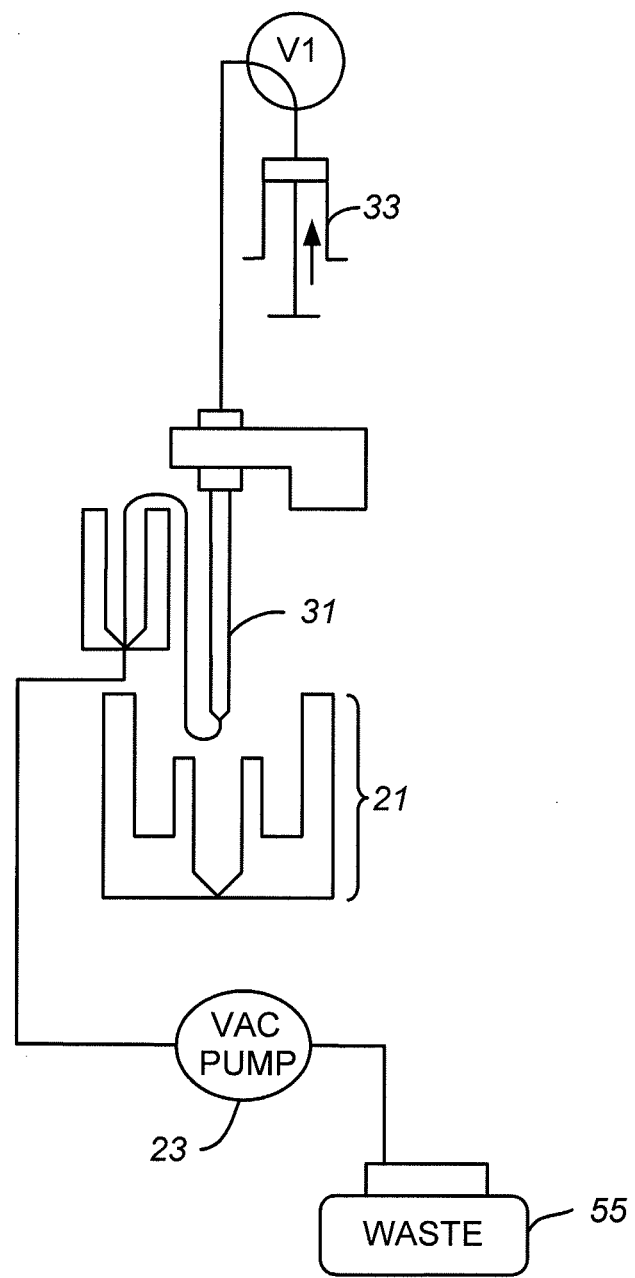
FIG. 5E is a diagram of the analyzer of FIG. 1 in a fifth stage of operation.

A flow configuration for washing the sample needle 31 is illustrated in FIG. 5E. To achieve this configuration, wash fluid from the wash fluid reservoir 43 is drawn into the first low-pressure pump 33, and once the pump is primed with the wash fluid, transition valve V1 is energized, the needle 31 is moved over to the needle wash well 22, the first low-pressure pump 33 is activated in the forward direction (a shown by the arrow), and the vacuum pump 23 is activated. Wash fluid then flows through the needle into the needle wash well 22, and is then drawn from the needle wash well 22 into the waste receptacle 55. This needle washing stage is performed after each sample to prevent the samples from contamination from previous samples.

Figure 5F:
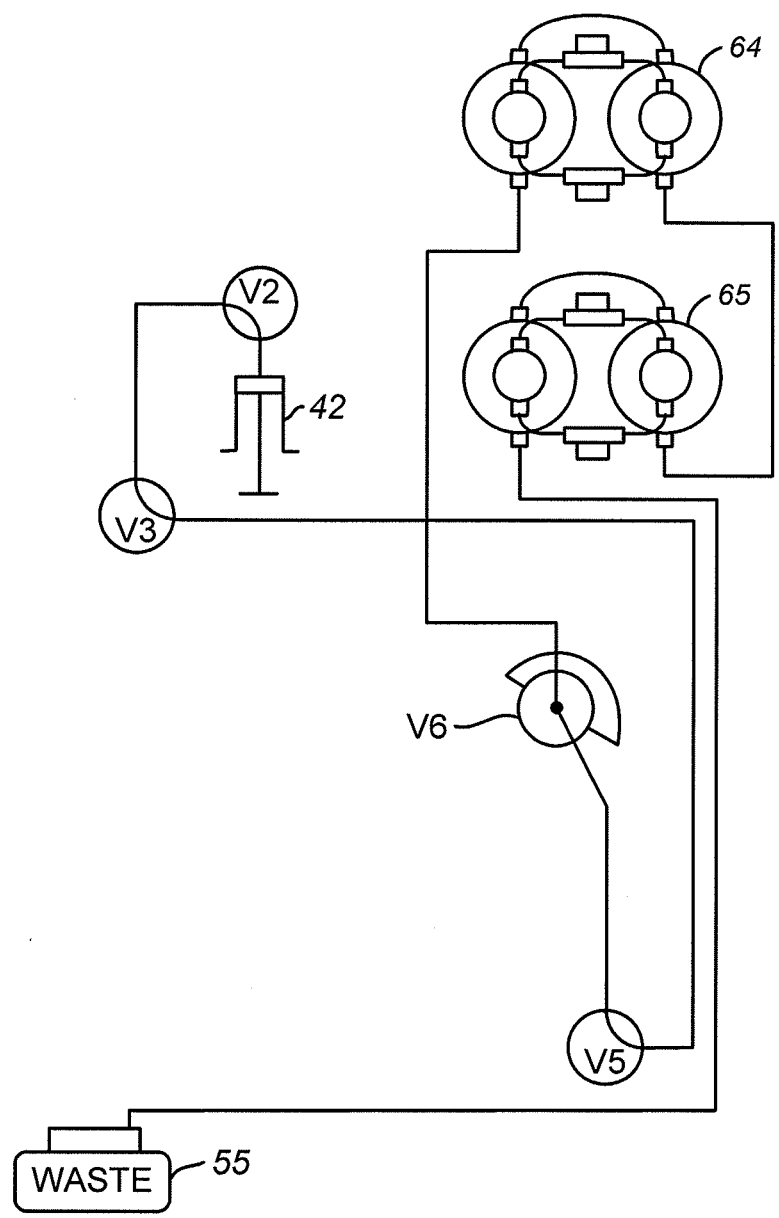
FIG. 5F is a diagram of the analyzer of FIG. 1 in a sixth stage of operation.

The final flow configuration, shown in FIG. 5F, is used for washing the backs of all four pistons of the high-pressure pumps 64, 65, using wash fluid drawn from the wash fluid reservoir 43 by the low-pressure pump 42. This wash removes salt crystals that are formed on the backs of the pistons when small amounts of buffer leak past the pump seals during the normal operation of the pumps. If allowed to remain, the salt crystals would reduce the life of a seal. In the configuration shown in FIG. 5F, the three-way valve V2 is energized and the injection valve V6 is rotated to a position in which port 76 is connected to port 77. Washing the backs of the pistons in this manner need not be performed after every sample, but best results are obtained when the wash is performed periodically, such as once a day.

Figure 6:
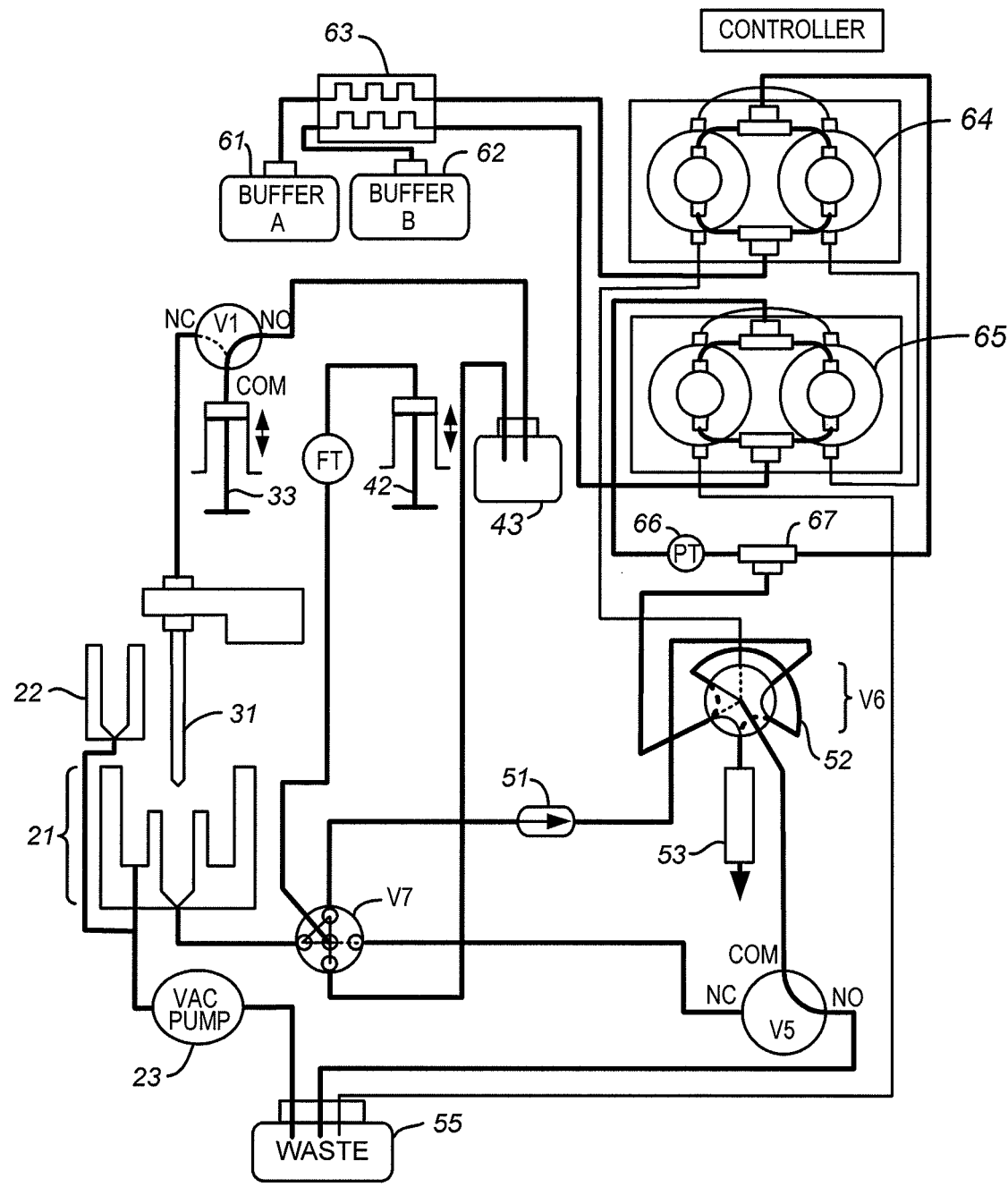
FIG. 6 is a diagram of an alternative flow system for an analyzer in accordance with the present invention.

The alternative system shown in FIG. 6 contains the same subsystems and components as the system of FIG. 2, except that one three-way valve V4 of FIG. 2 is replaced with a five-port rotary valve V7 and two other three-way valves V2 and V3 are eliminated. The stages shown in FIGS. 5A through 5F are nevertheless achieved by manipulation of the valves V1, V5, V6, and V7.

Figure 7:
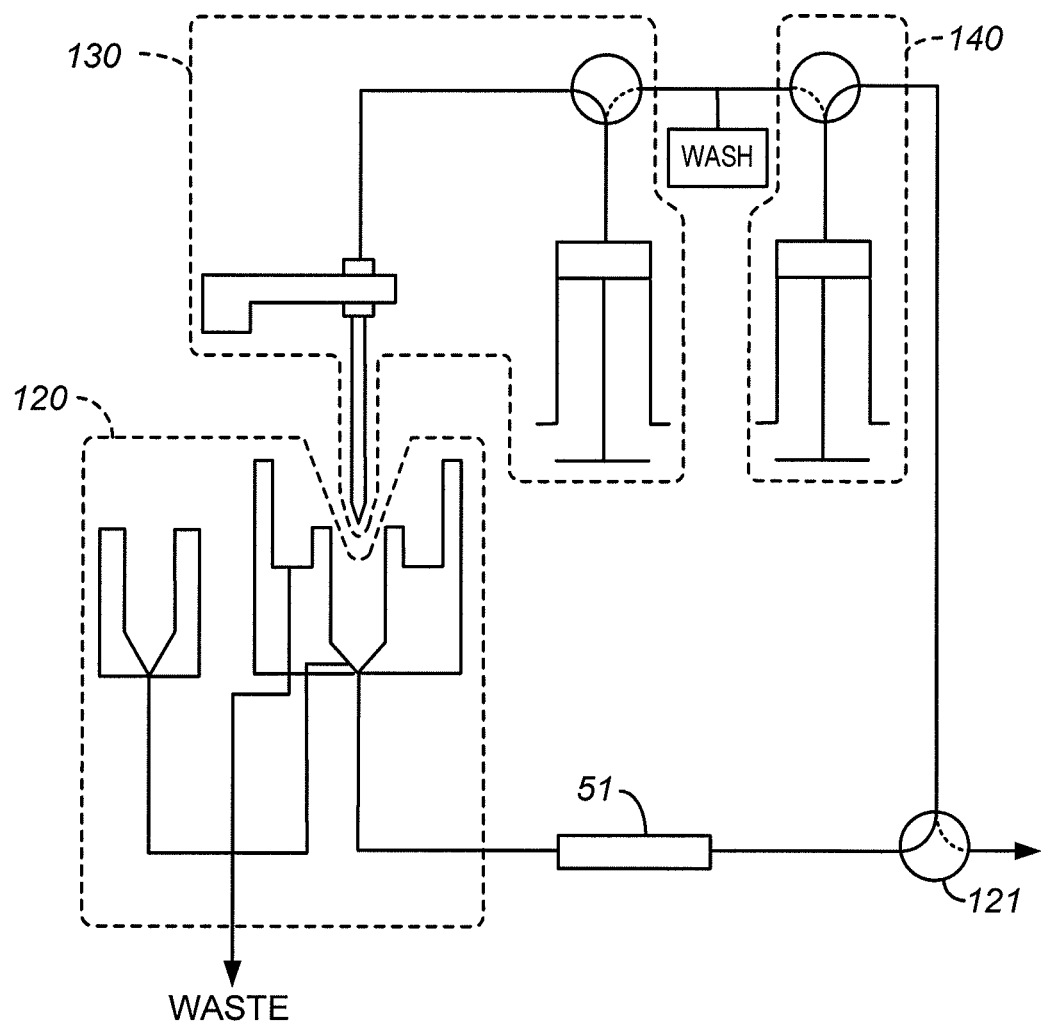
FIG. 7 is a diagram of a further alternative flow system for an analyzer in accordance with the present invention.

A further alternative for three of the subsystems is shown in FIG. 7. A dilution subsystem 120 in FIG. 7 serves the same function as the dilution subsystem 20 of FIG. 2; a sample transfer subsystem 130 in FIG. 7 serves the same function as the sample transfer subsystem 30 of FIG. 2; and a low-pressure pump system 140 in FIG. 7 serves the same function as the low-pressure pump system 40 of FIG. 2. Not shown in FIG. 7 are the analytical cartridge subsystem and the high-pressure pump subsystem; the corresponding subsystems of FIG. 2 can be used here, with appropriate connections that will be readily apparent to those of skill in the art. A feature of the system of FIG. 7 is the inclusion of a three-way valve 121 leading from the dilution subsystem 120 and the low-pressure pump system 140 to both the analytical cartridge subsystem and the high-pressure pump subsystem. The analytical cartridge subsystem and the high-pressure pump subsystem will be to the right of the valve 121 in the configuration shown in the drawing. The filter 51 is placed between the sample dilution subsystem 120 and the three-way valve 121, and no valves exist between the sample dilution subsystem 120 and the filter 51. The filter thus protects all valves from sample debris.

The low-pressure filter 51 is preferably a material with pores less than 1.0 micron in width, more preferably from about 0.1 micron to about 0.8 micron, and most preferably from about 0.2 micron to about 0.5 micron. While the pores will generally cover a range of sizes forming a pore size distribution curve, the widths quoted herein are those at the center or maximum of the curve. If the pores are cylindrical, the quoted width represents the diameters of the pores; if the pores are slits, the width represents the narrowest dimension of a given pore opening. The filter can be formed from one or more screens, or from one or more frits, or from packed particles. Screens, including mesh screens, offer the advantage of ease of cleaning. Examples of materials of construction for the filter are woven wire mesh, silver membranes, nylon membranes, polymer membranes, porous alumina membranes, sintered ceramic, plastic, and stainless steel. Examples of polymers from which membranes can be made are hydrophilic forms of PCTE (polycarbonate), PES (polyethersulfone), PVDF (polyvinyldifluoride), polypropylene, and PTFE (polytetrafluoroethylene). Layered mesh screens are also useful, since they can be used to form graduated pore sizes that either increase or decrease in the direction of flow. Other filter media that can be used are laser-microdrilled or photoetched metal foils.

The low-pressure filter is preferably mounted in a holder that secures the filter in place in the flow line, eliminates filter flexing when flexible filter material is used, and, when needed, promotes the distribution of the sample flow over the filter area to utilize the entire filter area. A patterned flow distribution can achieved by conventional means, including channels, baffles, and the like. A patterned flow distribution within the filter can enhance the ability of the backflush to clean the filter between samples. Cleaning efficiency can also be improved by appropriate selection of the locations of both the entrance of the flow into the filter and its exit from the filter. Directing sample flow across the surface of the filter, for example, in either straight or patterned flow paths will make cleaning of the filter more effective during backflush. Cleaning can also be enhanced by pulsing the backflush flow or by inducing turbulence, cavitation, or both by the application of ultrasonic energy. Filters and filter holders with structures that induce turbulence or that enhance high flow streaming will also improve the effectiveness of backflush.

The analyzer thus has a low-pressure subsystem and a high-pressure subsystem, with the prefilter in the former and the analytical cartridge in the latter. It is contemplated that in most cases the pressure at the low-pressure filter will be within the range of about 1 to about 30 psi (about 7 to about 206 kPa), while the pressure at the high-pressure side will be within the range of about 1,000 to about 10,000 psi (about 6,895 to about 68,947 kPa).

Backflushing can be performed after each sample injection or after two or more sample injections. With regular backflushing, the low-pressure filter can be used for as many as 10,000 injections, or in many cases preferably as many as 100,000 injections, and even as many as 1,000,000 injections. Downstream parts of the system that would otherwise deteriorate or become clogged by the debris, such as fluid passageways and valves, can likewise be used for 10,000 injections, and preferably 100,000 injections, or even 1,000,000 injections before needing removal and replacement. The analytical cartridge can be used for 1,000 injections, and preferably 10,000 injections, or most preferably 100,000 injections.

In the claims appended hereto, the team "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. An automated analyzer comprising:
    a low-pressure section comprising means for introducing sample to said analyzer, a sample dilution well for receiving a sample dilution fluid, and a low-pressure pump,
    a high-pressure section comprising a high-pressure pump,
    an analytical section comprising a sample loop and an analytical cartridge,
    a switching valve for switching between (i) connecting said low-pressure section to said sample loop of said analytical section and (ii) connecting said high-pressure section to said sample loop of said analytical section,
    a sample filter positioned in said low-pressure section, and
    a backflush pump arranged to back flush the sample filter at low pressure with a wash fluid, wherein the sample dilution fluid and the wash fluid are composed of the same solution.

2. The automated analyzer of claim 1 wherein the low-pressure section comprises means for producing pressure pulsations in said sample filter.

3. The automated analyzer of claim 1 wherein the low-pressure section comprises an ultrasonic transducer for producing ultrasonic pressure waves in said sample filter.

4. The automated analyzer of claim 1, further comprising a backflush pump, and wherein said switching valve further comprises (iii) a third position connecting said backflush pump with a sample loop at low pressure.

5. The automated analyzer of claim 1, wherein the backflush pump is arranged to back flush the sample loop and the sample filter.

6. The automated analyzer of claim 1, wherein the apparatus comprises a sample dilution subsystem in the low pressure section and no valves are present between the filter and the sample dilution subsystem.

7. An automated analyzer comprising:
   a sample dilution well,
   a sample transfer subsystem comprising (i) a needle mounted on a mobile needle arm movable into a position whereby said needle is in fluid communication with said sample dilution well, (ii) a pump arranged to cause fluid to pass through said needle, and (iii) a two-way switching valve switchable between communicating said pump with said needle and communicating said pump with a source of wash fluid,
   a sample loop and an analytical cartridge arranged to receive fluid emerging from said sample loop,
   a low-pressure pump subsystem arranged to pump diluted sample from said sample dilution well to said sample loop at a low pressure of from about 1 psi to about 30 psi,
   a high-pressure pump subsystem arranged to pump buffer liquid from a source of buffer liquid through said sample loop and said analytical cartridge at a high pressure of from about 1,000 psi to about 10,000 psi,
   a multi-position switching valve having positions comprising (i) a first position connecting said low-pressure pump subsystem with said sample dilution well and said sample loop and thereby arranged to introduce diluted sample from said sample dilution well into said sample loop at said low pressure, and (ii) a second position connecting said high-pressure pump subsystem to said sample loop and said analytical cartridge and thereby arranged to direct diluted sample from said sample loop through said analytical cartridge at said high pressure, and
   a sample filter positioned between said sample dilution well and said sample loop at a site maintained at said low pressure by said low-pressure pump subsystem at both of positions (i) and (ii) of said multi-position switching valve, and
   a backflush pump arranged to back flush the sample filter at low pressure.

8. The automated analyzer of claim 7 wherein said sample dilution well has an outlet and said sample filter is positioned between said outlet and all switching valves of said analyzer.

9. The automated analyzer of claim 7 wherein said sample filter comprises a mesh screen.

10. The automated analyzer of claim 7 wherein said sample filter comprises a silver membrane.

11. The automated analyzer of claim 7 wherein said sample filter comprises a nylon membrane.

12. The automated analyzer of claim 7 wherein said sample filter comprises pores of 0.1 micron to 0.8 micron in width.

13. The automated analyzer of claim 7 wherein said pump is a syringe pump operable to cause fluid to pass through said needle in either direction.

14. The automated analyzer of claim 7 wherein said low-pressure pump subsystem comprises a syringe pump operable to both draw fluid into an interior of said syringe pump and to expel fluid from said interior.

15. The automated analyzer of claim 7 wherein said multi-position switching valve positions further comprise (iii) a third position connecting said backflush pump with said source of wash fluid and said sample filter and thereby arranged to backflush said sample filter with wash fluid from said source of wash fluid at said low pressure.

16. The automated analyzer of claim 15 wherein said low-pressure pump subsystem comprises a low-pressure pump, and a common pump serves as both said low-pressure pump and said backflush pump.

17. The automated analyzer of claim 15 further comprising pressure means for producing pressure pulsations on said wash fluid passing through said sample filter.

18. The automated analyzer of claim 15 further comprising means for producing ultrasonic pressure waves in said wash fluid passing through said sample filter.

19. The automated analyzer of claim 7, wherein the backflush pump is arranged to back flush the sample loop and the sample filter.

20. A method for analyzing a sample of biological fluid by column chromatography, said method comprising:
   (A) introducing said sample into a low-pressure section of an automated analyzer, wherein said low-pressure section comprises a low-pressure pump and a sample dilution well for receiving a sample dilution fluid and said automated analyzer further comprises:
      a high-pressure section comprising a high-pressure pump,
      an analytical section comprising a sample loop and an analytical cartridge,
      a switching valve for switching between position (i) connecting said low-pressure section to said sample loop of said analytical section and position (ii) connecting said high-pressure section to said sample loop of said analytical section while closing off said low-pressure section from said analytical section,
      a sample filter positioned in said low-pressure section, and
      a backflush pump arranged to back flush the sample filter at low pressure with a wash fluid, wherein the sample dilution fluid and the wash fluid are composed of the same solution;
   (B) by way of said low-pressure pump, pumping said sample through said sample filter and into said sample loop with said switching valve in position (i); and
   (C) by way of said high-pressure pump, pumping said sample from said sample loop through said analytical cartridge with said switching valve in position (ii); and
   (D) detecting components of said sample separated from each other by said analytical cartridge.

21. The method of claim 20 further comprising backflushing said sample filter following step (D).

22. The method of claim 21 further comprising applying pressure pulsations to said sample filter during said backflushing or applying ultrasound vibrations to said sample filter during said backflushing.

23. An automated analyzer comprising:
   a low-pressure section comprising means for introducing sample to said analyzer, a sample dilution well for receiving a sample dilution fluid, and a low-pressure pump,
   a high-pressure section comprising a high-pressure pump,
   an analytical section comprising a sample loop and an analytical cartridge,
   switching means for switching between (i) connecting said low-pressure section to said sample loop of said analytical section and (ii) connecting said high-pressure section to said sample loop of said analytical section, a sample filter positioned in said low-pressure section and no valve exists between the sample dilution well and the filter, and a backflush pump arranged to back flush the sample filter at low pressure.

24. An automated analyzer comprising:

a sample dilution well, a sample transfer subsystem comprising (i) a needle mounted on a mobile needle arm movable into a position whereby said needle is in fluid communication with said sample dilution well, (ii) pump means arranged to cause fluid to pass through said needle, and (iii) a two-way switching valve switchable between communicating said pump means with said needle and communicating said pump means with a source of wash fluid, a sample loop and an analytical cartridge arranged to receive fluid emerging from said sample loop, a low-pressure pump subsystem arranged to pump diluted sample from said sample dilution well to said sample loop at a low pressure of from about 1 psi to about 30 psi, a high-pressure pump subsystem arranged to pump buffer liquid from a source of buffer liquid through said sample loop and said analytical cartridge at a high pressure of from about 1,000 psi to about 10,000 psi, a multi-position switching valve having positions comprising (i) a first position connecting said low-pressure pump subsystem with said sample dilution well and sample loop and thereby arranged to introduce diluted sample from said sample dilution well into said sample loop at said low pressure, and (ii) a second position connecting said high-pressure pump subsystem to said sample loop and said analytical cartridge and thereby arranged to direct diluted sample from said sample loop through said analytical cartridge at said high pressure, a sample filter positioned between said sample dilution well and said sample loop at a site maintained at said low pressure by said low-pressure pump subsystem at both of positions (i) and (ii) of said multi-position switching valve section and wherein no valve exists between the sample dilution well and the filter, and a backflush pump arranged to back flush the sample filter at low pressure.

25. A method for analyzing a sample of biological fluid by column chromatography, said method comprising:

(A) introducing said sample into a low-pressure section of an automated analyzer, wherein said low-pressure section comprises a low-pressure pump and a sample dilution well for receiving a sample dilution fluid and said automated analyzer further comprises:

a high-pressure section comprising a high-pressure pump, an analytical section comprising a sample loop and an analytical cartridge, a switching valve for switching between position (i) connecting said low-pressure section to said sample loop of said analytical section and position (ii) connecting said high-pressure section to said sample loop of said analytical section while closing off said low-pressure section from said analytical section, a sample filter positioned in said low-pressure section wherein no valve exists between the sample dilution well and the filter, and a backflush pump arranged to back flush the sample filter at low pressure;

(B) by way of said low-pressure pump, pumping said sample through said sample filter and into said sample loop with said switching valve in position (i); and (C) by way of said high-pressure pump, pumping said sample from said sample loop through said analytical cartridge with said switching valve in position (ii); and (D) detecting components of said sample separated from each other by said analytical cartridge.

26. The method of claim 25 further comprising backflushing said sample filter following step (D).

* * * * *